US009526862B2

(12) United States Patent
Iijima et al.

(10) Patent No.: US 9,526,862 B2
(45) Date of Patent: Dec. 27, 2016

(54) MEDICAL TUBE AND FLEXIBILITY-VARIABLE MECHANISM WITH THE SAME

(71) Applicants: Samsung Electronics Co., Ltd., Gyeonggi-do (KR); The University of Tokyo, Tokyo (JP)

(72) Inventors: Kazuo Iijima, Kanagawa (JP); Ken Masamune, Tokyo (JP); Takahiro Tokumiya, Kanagawa (JP); Siyang Zuo, Tokyo (JP)

(73) Assignees: Samsung Electronics Co., Ltd (KR); The University of Tokyo (JP)

( * ) Notice: Subject to any disclaimer, the term of this patent is extended or adjusted under 35 U.S.C. 154(b) by 64 days.

(21) Appl. No.: 14/139,014

(22) Filed: Dec. 23, 2013

(65) Prior Publication Data
US 2014/0188054 A1  Jul. 3, 2014

(30) Foreign Application Priority Data

Dec. 27, 2012  (JP) .................................. 2012-285254
Oct. 18, 2013  (KR) ......................... 10-2013-0124479

(51) Int. Cl.
  *A61M 31/00*  (2006.01)
  *A61M 25/00*  (2006.01)
  *A61M 25/01*  (2006.01)

(52) U.S. Cl.
  CPC ...... *A61M 25/0052* (2013.01); *A61M 25/0144* (2013.01); *A61M 2025/0003* (2013.01)

(58) Field of Classification Search
  CPC ................. A61M 2025/0003; A61M 25/0052; A61M 25/0144

(Continued)

(56) References Cited

U.S. PATENT DOCUMENTS 5,916,147 A * 6/1999 Boury ........................... 600/146
8,262,563 B2 * 9/2012 Bakos et al. .................. 600/141
(Continued)

FOREIGN PATENT DOCUMENTS

| JP | 2007511247 | 5/2007 |
| WO | WO9219147 | 11/1992 |
| WO | WO2009107792 | 9/2009 |

*Primary Examiner* — Kevin C Sirmons
*Assistant Examiner* — Deanna K Hall
(74) *Attorney, Agent, or Firm* — The Farrell Law Firm, P.C.

(57) ABSTRACT

A medical tube which is highly flexible and has a very small diameter and a flexibility-variable mechanism having the medical tube are provided. The medical tube includes an interior tube and a plurality of annular segments of a cylindrical shape into which the interior tube is inserted. The medical tube is configured by sequentially connecting the plurality of annular segments while the interior tube is inserted inside of the plurality of annular segments. Each annular segment includes a fitting portion that allows any other annular segment to be fitted to the annular segment, and a fitted portion which may be fitted on the fitting portion of any other annular segment, which has a diameter that increases toward an end of the annular segment and includes at least one slit extending in a direction crossing a diametric direction. When the spacing of the slit is narrowed, the fitting portion of the annular segment and the fitted portion of any other annular segment are engaged with each other so that the annular segments are fixed to each other.

7 Claims, 8 Drawing Sheets

(58) Field of Classification Search
USPC .................................... 604/525, 535, 95.04
See application file for complete search history.

(56) References Cited

U.S. PATENT DOCUMENTS

| | | |
|---|---|---|
| 2010/0324370 A1 | 12/2010 | Dohi et al. |
| 2012/0179097 A1* | 7/2012 | Cully et al. ................ 604/95.05 |
| 2013/0253537 A1 | 9/2013 | Saadat et al. |

* cited by examiner

MEDICAL TUBE AND FLEXIBILITY-VARIABLE MECHANISM WITH THE SAME

PRIORITIES

This application claims priority under 35 U.S.C. §119(a) to Japanese Application Serial No. JP 2012-285254, which was filed in the Japanese Patent Office on Dec. 27, 2012, and to Korean Application Serial No. KR 10-2013-0124479, which was filed in the Korean Patent Office on Oct. 18, 2013, the entire contents of each of which are incorporated herein by reference.

BACKGROUND OF THE INVENTION

1. Field of the Invention

The present invention relates to a medical tube and a flexibility-variable mechanism.

2. Description of the Related Art

Japanese National Phase Patent Laid-Open Publication No. 2007-511247 discloses a flexibility/rigidity-variable device that includes a tube which is an elongated member, a projection (engaging abutment) provided on the outer circumference of the tube, an engaging portion which is engageable with the projection, a sealing cover that covers the outer circumference of the tube, and a fluid inlet/outlet portion connected to a sealed space between the sealing cover and the tube. This reference describes a medical tube in which, when the air within the sealed space is discharged from the inlet/outlet portion to the outside, the engaging portion may be engaged with the projection of the tube and the shape of the tube may remain in a fixed state.

Japanese National Phase Patent Laid-Open Publication No. 1994-511163 discloses a medical tube in which a main body to be inserted into the inside of a patient's body has a deflectable or steerable shaft, and the shaft is provided with a plurality of elements which may be engaged with each other. This reference describes that each element is provided with, for example, a lumen through which a pull wire extends and a scope lumen at the center thereof, and when a tension is applied to the pull wire, the elements are pressed so that the shaft may be fixed at a predetermined position.

Japanese National Phase Patent Laid-Open Publication No. 2009-107792 discloses a flexibility-adjustable exploration device having an inner duct and an outer duct. This reference describes that the inner duct is configured by a plurality of cylindrical segments which are connected in series and bound by a flexible cable. Further, this reference describes that, when elasticity is given to the cable, the respective segments are fixed and not to be moved by frictional force.

However, the first two references have a problem in that because the shaft or the inner duct is fixed using a wire, the diameter of a portion to be inserted into a patient's body is increased.

For flexibility of a medical tube, it is necessary to control the medical tube such that the medical tube is in a fixed state in which it is somewhat flexible depending on a medical treatment portion. However, the medical tubes described in the first two references have a problem in that it is impossible to control the medical tubes to be in such a fixed state.

In addition, the third reference has a problem in that because a high rigid support member is provided along the longitudinal direction of the tube, the flexibility varies depending on the curved (bent) direction of the tube. That is, the ducts disclosed in this reference have a problem regarding anisotropy in terms of flexibility.

SUMMARY OF THE INVENTION

The present invention has been made to address at east the above problems and/or disadvantages and to provide at least the advantages described below.

According to an aspect of the present invention, a medical tube is provided, which includes an interior tube and a plurality of annular segments of a cylindrical shape into which the interior tube may be inserted. The medical tube includes an interior tube and a plurality of annular segments of a cylindrical shape into which the interior tube may be inserted. The medical tube is configured by sequentially connecting the plurality of annular segments while the interior tube is inserted into the inside of the plurality of annular segments. Each annular segment includes a fitting portion that allows any other annular segment to be fitted to the annular segment, and a fitted portion which may be fitted on the fitting portion of any other annular segment. The fitting portion of each annular segment has a diameter that increases toward an end of the annular segment and includes at least one slit extending in a longitudinal direction. When the spacing of the slit of the fitting portion of each annular segment is narrowed, the fitting portion of the annular segment and the fitted portion of any other annular segment are engaged with each other so that the annular segments are fixed to each other.

According to another aspect of the present invention, a flexibility-variable mechanism is provided, which includes a medical tube comprising a tubular sheath tube installed around a tube that is formed by sequentially connecting the plurality of annular segments including at least one slit, and an inside pressure control unit that controls the inside pressure between the interior tube and the sheath tube. When the inside pressure control unit lowers the inside pressure between the interior tube and the sheath tube below the outside pressure of the sheath tube, the spacing of each slit of the annular segments is narrowed, the plurality of the annular segments are engaged with each other, and the shape of the medical tube is fixed. In addition, when the inside pressure control unit makes the inside pressure between the interior tube and the sheath tube substantially equal to the outside pressure, the spacing of each slit of the annular segments returns to normal, the engagement of the plurality of annular segments is released, and the medical tube is made to be bendable.

BRIEF DESCRIPTION OF THE DRAWINGS

The above and other aspects, features, and advantages of certain embodiments of the present invention will be more apparent from the following detailed description taken in conjunction with the accompanying drawings, in which.

DETAILED DESCRIPTION OF EMBODIMENTS OF THE PRESENT INVENTION

Hereinafter, various embodiments of the present disclosure will be described with reference to the accompanying drawings. In the following description of the present disclosure, a detailed description of known functions and configurations incorporated herein will be omitted when it may make the subject matter of the present disclosure unclear.

1. First Exemplary Embodiment

Figure 1:
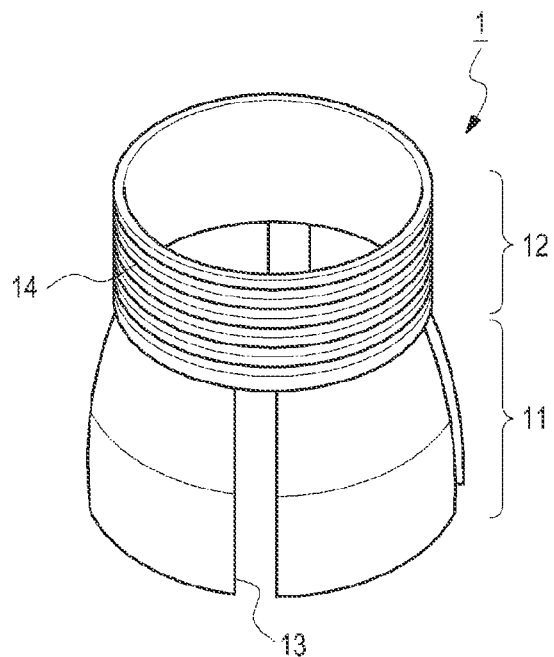
FIG. 1 is a perspective view illustrating an annular segment of a medical tube according to a first embodiment of the present invention.
Figure 2:
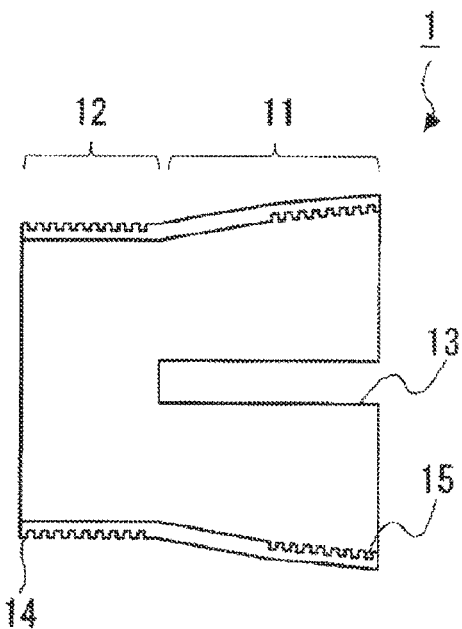
FIG. 2 is a cross-sectional view illustrating the annular segment of the medical tube according to the first embodiment of the present invention.
Figure 3A:
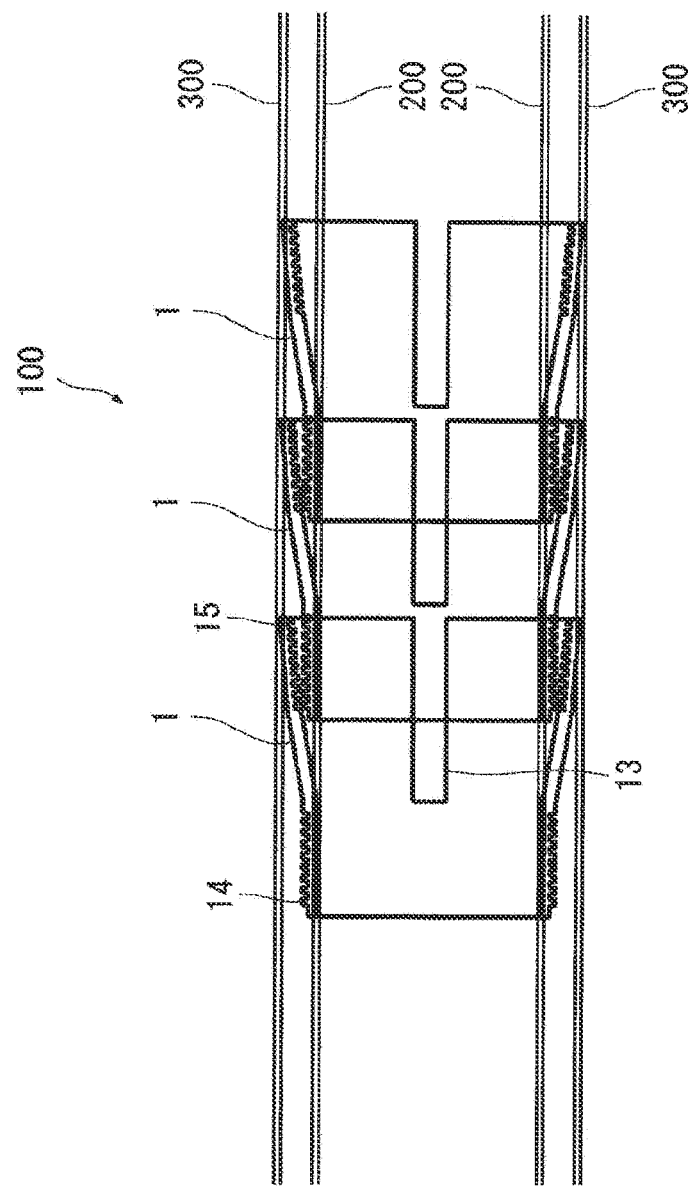
FIG. 3A is a cross-sectional view illustrating a state in which the annular segments according to the first embodiment of the present invention are connected.
Figure 3B:
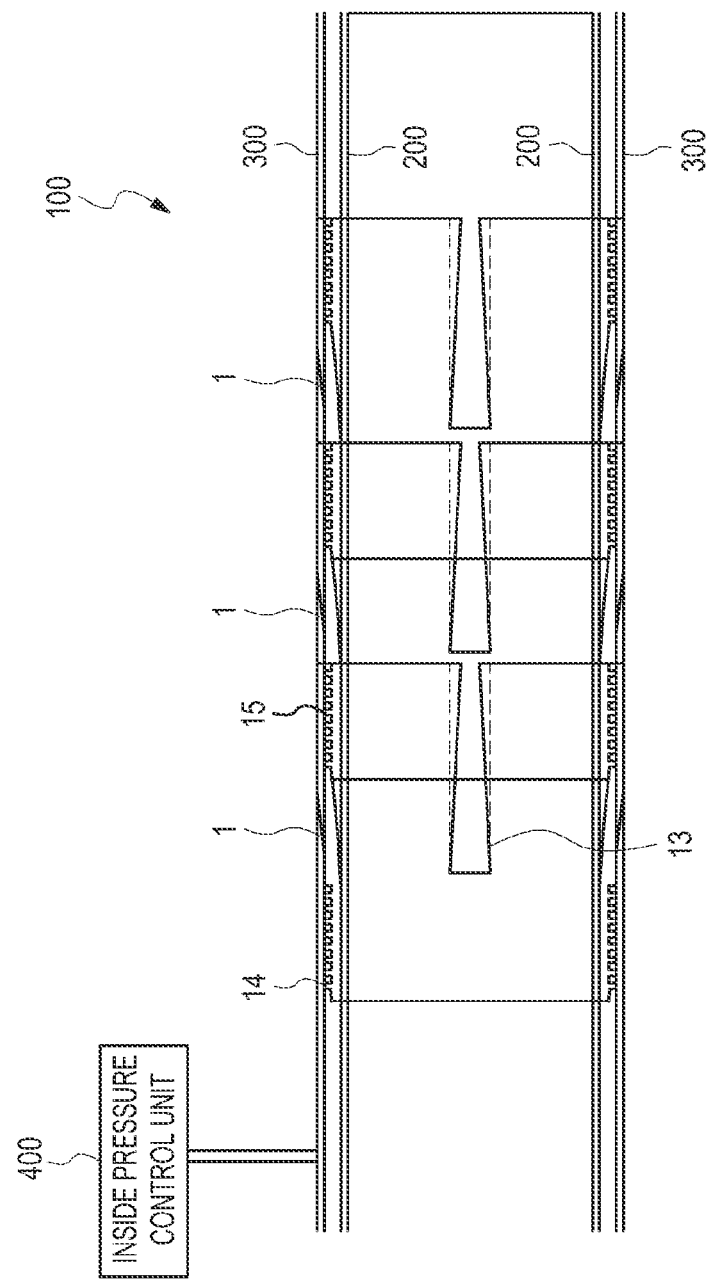
FIG. 3B is a cross-sectional view illustrating states in which the annular segments according to the first embodiment of the present invention are connected.

A configuration of a medical tube 100 according to the first embodiment of the present invention will be described with reference to FIGS. 1 to 3B. FIG. 1 is a perspective view illustrating an annular segment 1 of the medical tube 100 according to the first embodiment. FIG. 2 is a cross-sectional view illustrating the annular segment 1 of the medical tube 100 according to the first embodiment. FIGS. 3A and 3B are cross-sectional views illustrating states in which the annular segments 1 according to the first embodiment are connected.

As illustrated in FIGS. 3A and 3B, the medical tube 100 includes an interior tube 200, and a plurality of annular segments 1 of a cylindrical shape into which the interior tube 200 is inserted. The medical tube 100 is configured by sequentially interconnecting the plurality of annular segments 1 while inserting the interior tube 200 into the annular segments 1.

Specifically, as illustrated in FIGS. 3A and 3B, the interior tube 200 is inserted into a cylindrical hole of each annular segment 1. In addition, the plurality of annular segments 1 are connected with each other while inserting the interior tube 200 into the cylindrical holes of the annular segments 1.

As illustrated in FIGS. 3A and 3B, the medical tube 100 further includes a tubular sheath tube 300 installed around a tube formed by interconnecting the plurality of annular segments 1. In other words, the sheath tube 300 covers the outer circumference of the tube formed by interconnecting the plurality of annular segments 1.

The interior tube 200 and the sheath tube 300 are formed of a bendable material. Further, the sheath tube 300 is formed of a material which may be inserted into a patient's body.

In addition, as will be described below, the medical tube 100 is bendable when the plurality of annular segments 1 are connected without being fixed to each other, and when the annular segments 1 are connected to be fixed to each other, the shape of the medical tube 100 is fixed.

For fabricating the annular segments 1, various conventional methods may be used according to a material which is used for the annular segments 1. The fabricating methods are not especially limited, and for example, various resins and metals may be used. For example, the annular segments 1 may be fabricated by molding or machining.

As illustrated in FIGS. 1 and 2, each annular segment 1 is provided with a fitting portion 11 which allows any other annular segment 1 to be fitted to the inside of the corresponding annular segment 1, and a fitted portion 12 which may be fitted on the fitting portion 11 of any other annular segment 1.

The diameter of the fitting portion 11 increases toward an end of the annular segment 1. In addition, the fitting portion 11 includes at least one slit 13 extending in a direction crossing the diametrical direction, in other words, in the longitudinal direction of the interior tube 200.

In the first embodiment, two slits 13 are provided. However, the shape and the number of the slits 13 are not limited to the present embodiment.

In addition, the annular segment 1 is formed of a flexible material which allows the spacing of the slits 13 of the fitting portion 11 to be narrowed or to return to normal.

FIG. 3A illustrates a state in which the annular segments 1 are connected with each other without being fixed to each other, and FIG. 3B illustrates a state in which the annular segments 1 are connected with each other to be fixed to each other. FIGS. 3A and 3B are simplified views in which FIG. 3A illustrates a state in which the spacing of each slit 13 of the fitting portions 11 of the annular segments 1 is not narrowed. Meanwhile, FIG. 3B illustrates a state in which the spacing of each slit 13 of the fitting portions 11 of the annular segments 1 is narrowed.

As illustrated in FIGS. 3A and 3B, when the slits 13 of the fitting portions 11 of the annular segments 1 are narrowed, the fitting portion 11 of each annular segment 1 is engaged with the fitted portion 12 of any other annular segment 1 so that the annular segments 1 are fixed to each other.

More specifically, the fitted portion 12 of each annular segment 1 is provided with a plurality of protrusions 14 on the outer surface thereof along the cylindrical circumferential direction of the annular segment 1. In addition, the fitting portion 11 of the annular segment 1 is provided with a plurality of recesses 15 on the inner surface thereof which are capable of being engaged with the protrusions 14 of any other annular segment 1. As illustrated in FIGS. 3A and 3B, when the slits 13 of the fitting portion 11 of the annular segments 1 are narrowed, the plurality of protrusions 14 of the fitted portion 12 of one annular segment 1 and the plurality of recesses 15 of the fitting portion 11 of any other annular segment 1 are engaged with each other. With this arrangement, the annular segments 1 are fixed to each other.

Meanwhile, the shape of the recesses 15 of the fitting portion 11 and the protrusions 14 of the fitted portion 12 are merely examples of shapes that allow the annular segments 1 to be engaged with each other. For this reason, the shapes of the engaging surfaces of the fitting portion 11 and the fitted portion 12 are not limited to the present embodiment. Also, the recesses 15 of the fitting portions 11 and the protrusions 14 of the fitted portions 12 may not be provided along the circumferential direction of the annular segments 1.

In addition, the engagement force between the annular segments 1 may be adjusted by adjusting the depth of the recesses 15 of the fitting portions 11 and the height of the protrusions 14 of the fitted portions 12. Further, the engagement force between the annular segments 1 may be adjusted by adjusting the length of the recesses 15 provided on the fitting portions 11 and the length of the protrusions 14 of the fitted portions 12.

Further, the flexibility-variable mechanism according to the first embodiment includes the medical tube 100 as described above and an inside pressure control unit 400 that controls the inside pressure between the interior tube 200 and the sheath tube 300, which will be described below.

When the inside pressure control unit 400 lowers the inside pressure between the interior tube 200 and the sheath tube 300 below the outside pressure of the sheath tube 300, the spacing of each slit 13 of the annular segments 1 is reduced, the plurality of annular segments 1 are engaged with each other, and the shape of the medical tube 100 is fixed.

Meanwhile, when the inside pressure control unit 400 makes the inside pressure between the interior tube 200 and the sheath tube 300 substantially equal to the outside pressure, the spacing of each slit 13 of the annular segments 1 returns to normal, the engagement between the plurality of annular segments 1 is released, and the medical tube 100 is then bendable.

The inside pressure control unit 400 controls the inside pressure between the interior tube 200 and the sheath tube 300, for example, by allowing a fluid (e.g., gas or liquid) to go into or out of the space between the interior tube 200 and sheath tube 300. In addition, the control unit is one example of a mechanism that can control the narrowing of the slits 13 of the annular segments 1 or returning the slits 13 of the annular segments back to normal. Accordingly, the flexibility-variable mechanism may be configured such that the spacing of each slit 13 of the annular segments 1 is narrowed by being pressed from the outer circumference side of the sheath tube 300 instead of providing the inside pressure control unit.

As described above, the medical tube 100 according to the first embodiment of the present invention is provided with an interior tube and a plurality of annular segments 1 of a cylindrical shape into which the interior tube 200 is inserted. In addition, the medical tube 100 is configured by sequentially connecting the plurality of annular segments 1 while inserting the interior tube 200 into the annular segments 1. In other words, the medical tube 100 is configured by sequentially mounting the plurality of the annular segments 1 on the interior tube 200 so that the interior tube 200 is inserted into the inside of the annular segments 1 of the medical tube 100. In addition, each annular segment 1 includes a fitting portion 11 that allows any other annular segment 1 to be engaged in the inside of the annular segment 1, and a fitted portion 12 that is fitted on a fitting portion 11 of any other annular segment 1. The diameter of the fitting portion 11 increases toward an end of the annular segment 1 and the fitting portion 11 is provided with at least one slit 13 extending in a direction crossing the diametrical direction.

When the spacing of the slit 13 of the fitting portion 11 of an annular segment 1 is narrowed, the fitting portion 11 of the annular segment 1 and the fitted portion 12 of the other annular segment 1 fitted to the annular segment 1 are engaged with each other, the annular segments 1 are fixed to each other, and the medical tube becomes rigid.

With this arrangement, the shape of the medical tube 100 may be fixed merely by allowing the annular segments 1 to be engaged with each other without installing a drive wire to the medical tube 100 or providing a portion to be engaged with a high rigid support on the outer circumference of the interior tube 200. Thus, it is possible to provide a flexibility-variable medical tube 100 which is highly flexible and has a very small diameter.

In addition, the flexibility-variable mechanism according to the first embodiment includes a medical tube 100 provided with a tubular sheath tube 300 installed around a tube formed by sequentially connecting a plurality of annular segments 1, and an inside pressure control unit 400 that controls the inside pressure between an interior tube 200 and the sheath tube 300. In addition, when the inside pressure control unit 400 lowers the inside pressure between the interior tube 200 and the sheath tube 300, the spacing of each slit 13 of the annular segments 1 is narrowed, the plurality of annular segments 1 are engaged with each other, and the shape of the medical tube 100 is fixed. Meanwhile, when the inside pressure control unit 400 makes the inside pressure between the interior tube 200 and the sheath tube 300 substantially equal to the outside pressure, the spacing of each slit 13 of the annular segments 1 returns to normal, the engagement between the plurality of annular segments 1 is released, and the medical tube 100 is made to be bendable.

With this arrangement, the flexibility of the medical tube 100 may be controlled merely by controlling the inside pressure between the interior tube 200 and the sheath tube 300. In other words, with an easier configuration, the flexibility of the medical tube 100 may be controlled.

2. Second Exemplary Embodiment

Figure 4:
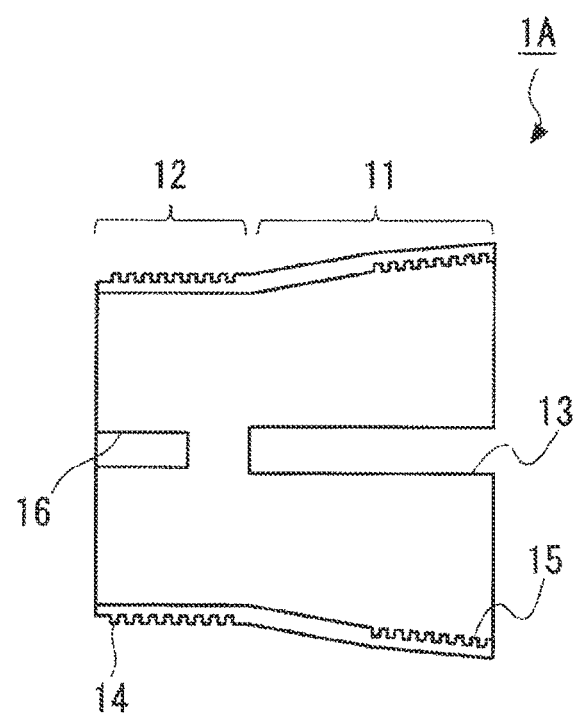
FIG. 4 is a cross-sectional view illustrating an annular segment 1A of a medical tube according to a second embodiment of the present invention.
Figure 5A:
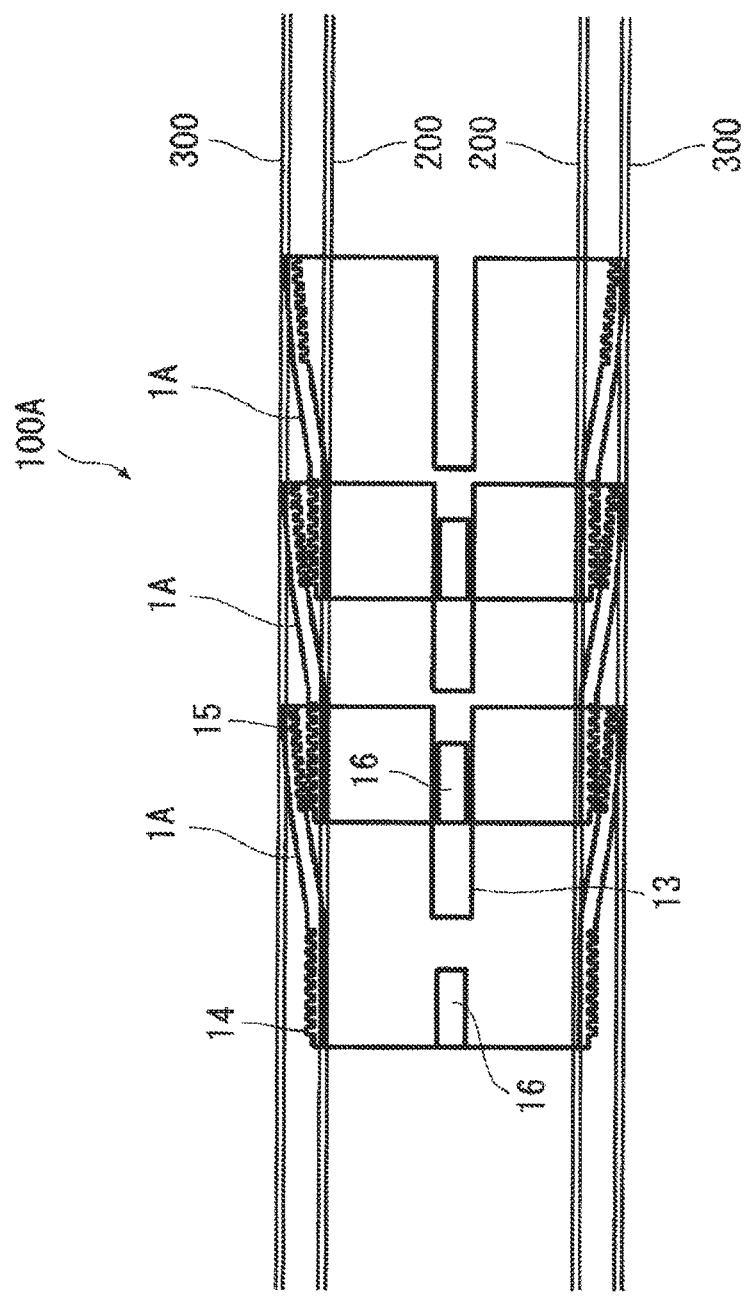
FIG. 5A illustrates a state in which the annular segments according to the second embodiment of the present invention are connected with any other.
Figure 5B:
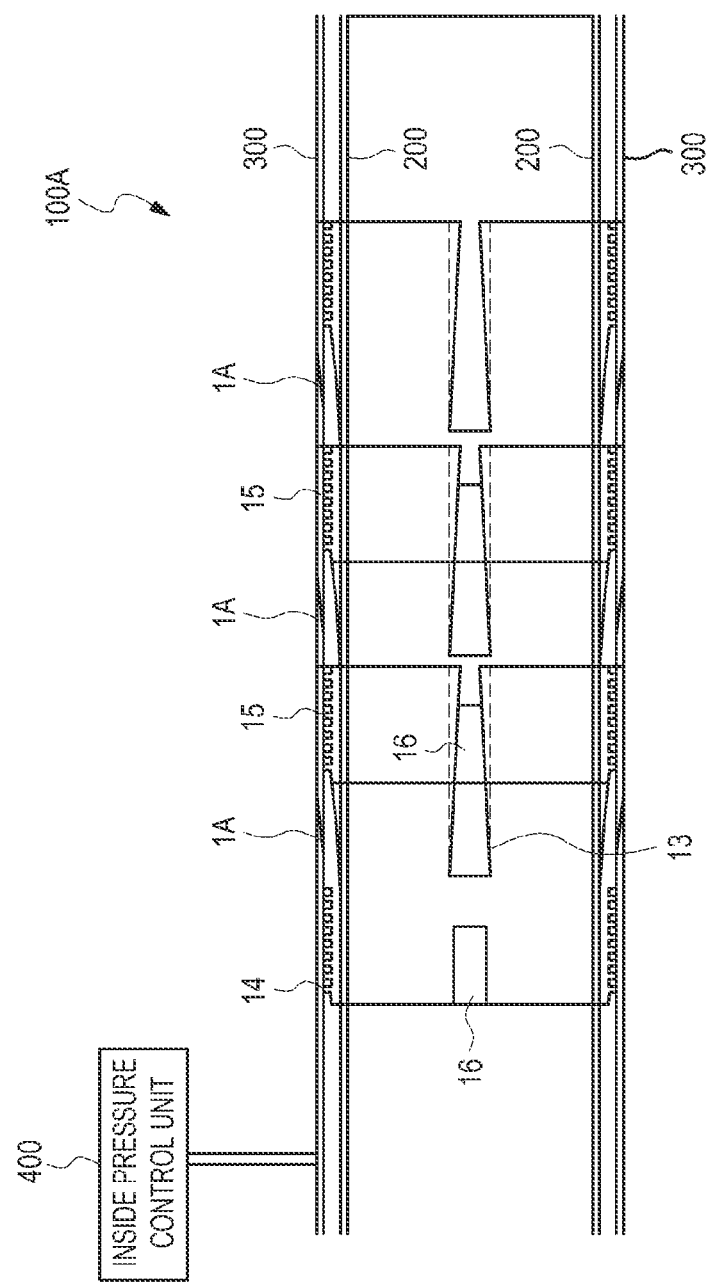
FIG. 5B illustrates a state in which the annular segments according to the second embodiment of the present invention are connected with any other.

A configuration of a medical tube 100A according to a second embodiment will be described with reference to FIGS. 4, 5A and 5B. FIG. 4 is a cross-sectional view illustrating an annular segment 1A of a medical tube 100A according to the second embodiment of the present invention. FIGS. 5A and 5B are cross-sectional views illustrating states in which the annular segments 1A are connected with each other. Specifically, FIG. 5A illustrates a state in which the annular segments 1 are connected with each other without being fixed to each other, and FIG. 5B illustrates a state in which the annular segments 1 are connected with each other so as to be fixed to each other.

As illustrated in FIGS. 4, 5A and 5B, the medical tube 100A according to the second exemplary embodiment is different from the medical tube 100 according to the first exemplary embodiment in that each annular segment 1A further includes a projection 16. Accordingly, the same elements will be assigned with the same reference numerals and a repetitive description thereof will be omitted.

The fitted portion 12 of each annular segment 1A is provided with a projection 16 which may be inserted into a slit 13 of any other annular segment 1A. The projection 16 may have any shape as long as it may be inserted into the slit 13. In addition, the height of the projection 16 is raised to such an extent that the projection 16 protrudes over the outer surface of the portion where the slit 13 of the fitting portion 11 is formed. Therefore, when one annular segment 1A and any other annular segment 1A are connected, the projection 16 of one annular segment 1A is inserted into the slit 13 of the other annular segment 1A so that the projection 16 is caught by the slit 13, thereby preventing rotation of the annular segments 1A with respect to an adjacent one of the annular segment 1A.

Further, the projection 16 may have any shape as long as it is formed to be inserted into the slit 13 and caught by the slit 13, and thus is not limited to the present embodiment.

According to the second embodiment, when one annular segment 1A and any other annular segment 1A are connected, the projection 16 of one annular segment 1A and the slit 13 of the other annular segment 1A are engaged so that the projection 16 is caught by the slit 13. As a result, rotation of the annular segments 1A may be prevented. In other words, when a rotation torque is applied to the medical tube 100A, rotation between annular segments 1A may be prevented so that a following performance of the medical tube 100A in relation to the rotation torque may be improved.

3. Third Exemplary Embodiment

Figure 6:
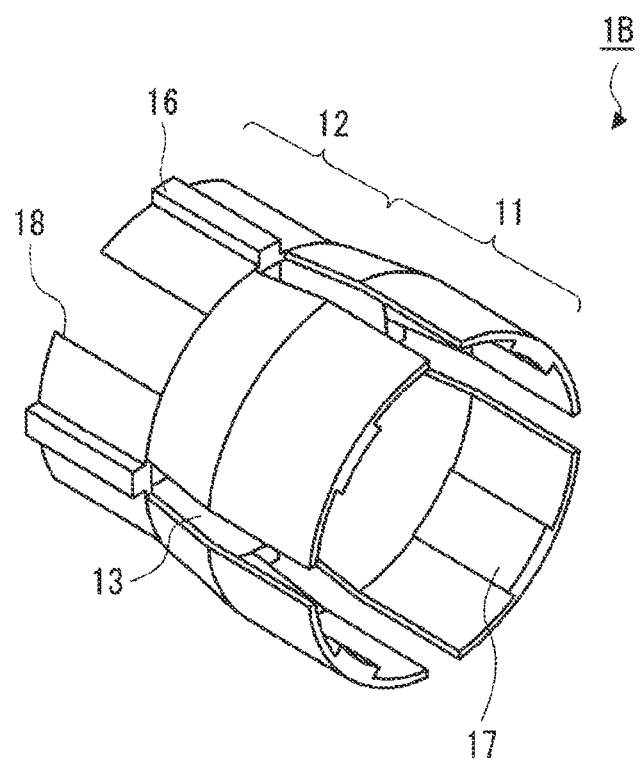
FIG. 6 is a perspective view illustrating an annular segment of a medical tube according to a third embodiment of the present invention.
Figure 7:
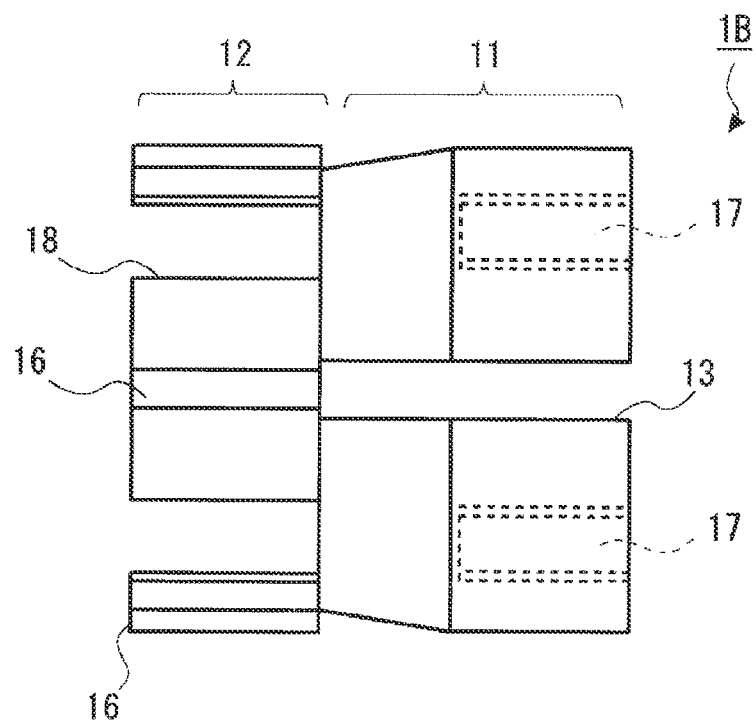
FIG. 7 is a side view illustrating the annular segment of the medical tube according to the third embodiment of the present invention.

A configuration of a medical tube according to a third embodiment will be described with reference to FIG. 6. FIG. 6 is a perspective view illustrating an annular segment 1B of the medical tube according to the third embodiment of the present invention. FIG. 7 is a side view illustrating the annular segment 1B of the medical tube according to the third embodiment.

As illustrated in FIGS. 6 and 7, the medical tube according to the third embodiment is different from the medical tube 100A according to the second embodiment in that the annular segment 1B is provided with protrusion portions 17 and insertion slits 18. Accordingly, the same elements will be assigned with the same reference numerals and a repetitive description thereof will be omitted.

The fitting portion 11 of the annular segment 1B is provided with protrusion portions 17 protruding from the inner surface of the annular segment 1B.

In addition, the fitted portion 12 of the annular segment 1B is provided with insertion slits 18 into which the protrusion portions 17 of any other annular segment 1B may be inserted.

The protrusion portions 17 protrude from the inner surface of the fitting portion 11 to have a width and a length capable of being inserted into the insertion slits 18 in FIGS. 6 and 7. In FIGS. 6 and 7, each of the protrusion portions 17 is formed substantially in a rectangular shape. However, the protrusion portions 17 may have any shape as long as they may be inserted into the insertion slits 18, and thus are not limited to the present embodiment.

Each insertion slit 18 is a portion where the fitted portion 12 is cut out from an end of the annular segment 1B substantially in a rectangular shape. The insertion slits 18 are formed to have a width and a length which allow the protrusion portions 17 to be inserted into the insertion slits 18. The insertion slits 18 may have any shape as long as they may allow the protrusion portions 17 to be inserted into the insertion slits 18, and thus are not limited to the present embodiment.

According to the present invention, it is possible to provide a flexibility-variable medical tube which is highly flexible and has a very small diameter.

Although the present invention has been described above in detail with reference to certain embodiments, the present invention is not limited to the embodiments as described above and various modifications may be made within the scope of the present invention.

What is claimed is:
1. A medical tube comprising:
an interior tube; and
a plurality of annular segments of a cylindrical shape into which the interior tube may be inserted,
wherein the medical tube is configured by sequentially connecting the plurality of annular segments while the interior tube is inserted inside of the plurality of annular segments,
wherein each annular segment includes a fitting portion that allows any other annular segment to be fitted to the annular segment, and a fitted portion which may be fitted on the fitting portion of any other annular segment,
wherein the fitting portion of each annular segment has a diameter that increases toward an end of the annular segment and includes at least one slit extending the entire length of the fitting portion in a longitudinal direction, and
wherein a spacing of the slit is configured to be narrowed or to return to normal,
when the spacing of the slit of the fitting portion of each annular segment is narrowed, the fitting portion of the annular segment and the fitted portion of any other annular segment are engaged with each other so that the annular segments are fixed to each other, and
when the spacing of the slit of the fitting portion of each annular segment returns to normal, the annular segments are connected with each other without being fixed to each other.

2. The medical tube of claim 1, wherein the fitted portion of each annular segment includes at least one protrusion on an outer surface thereof along a cylindrical circumferential direction thereof, and the fitting portion of each annular segment includes at least one recess on an inner surface thereof which are capable of being engaged with the at least one protrusion of any other annular segment.

3. The medical tube of claim 1, wherein the fitted portion of each annular segment includes a projection capable of being inserted into the slit of any other annular segment.

4. The medical tube of claim 1, wherein the fitting portion of each annular segment includes a protrusion portion that protrudes from an inner surface thereof and the fitted portion of each annular segment includes an insertion slit into which the protrusion portion of any other annular segment is capable of being inserted.

5. The medical tube of claim 1, further comprising:
a tubular sheath tube installed around the sequentially connected plurality of annular segments.

6. The medical tube of claim 5, further comprising an inside pressure control unit to control the inside pressure between the interior tube and the tubular sheath tube.

7. The medical tube of claim 6, wherein, when the inside pressure control unit lowers the inside pressure between the interior tube and the tubular sheath tube below the outside pressure of the tubular sheath tube, the spacing of each slit of the annular segments is narrowed, the plurality of the annular segments are engaged with each other, and the shape of the medical tube is fixed, and
when the inside pressure control unit makes the inside pressure between the interior tube and the tubular sheath tube substantially equal to the outside pressure, the spacing of each slit of the annular segments returns to normal, the engagement of the plurality of annular segments is released, and the medical tube is made to be bendable.

* * * * *